United States Patent [19]

Christiaens et al.

[11] Patent Number: 5,927,853
[45] Date of Patent: Jul. 27, 1999

[54] METHOD FOR THERMAL IMPEDANCE EVALUATION OF PACKAGED SEMICONDUCTOR COMPONENTS

[76] Inventors: Filip Christiaens, Weerstraat 78,2880, Bornem, Belgium; Luc Tielemans, Am Stein 6,52152, Simmerath, Germany; Luc De Schepper, Zestien-Bundersstrat 15,3500, Hasselt; Eric Beyne, Rotspoelstraat 15,3001, Heverlee, both of Belgium

[21] Appl. No.: 08/757,238

[22] Filed: Nov. 27, 1996

Related U.S. Application Data

[62] Division of application No. 08/543,867, Oct. 19, 1995, Pat. No. 5,795,063.
[60] Provisional application No. 60/003,899, Sep. 18, 1995.

[30] Foreign Application Priority Data

| Oct. 19, 1994 | [BE] | Belgium | ............................... 09400949 |
| Sep. 18, 1995 | [BE] | Belgium | ................. PCT/BE95/00085 |

[51] Int. Cl.$^6$ ........................... G01N 25/20; G01N 25/18
[52] U.S. Cl. ................................................. 374/43; 374/44
[58] Field of Search .................... 374/43, 44, 57

[56] References Cited

U.S. PATENT DOCUMENTS

| 2,587,622 | 3/1952 | Jaffe | ........................................... 374/43 |
| 3,045,473 | 7/1962 | Hager, Jr. | ................................... 374/44 |
| 3,242,716 | 3/1966 | Webb | ........................................ 374/44 |
| 3,572,093 | 3/1971 | Butler, Jr. et al. | ......................... 374/44 |
| 3,745,460 | 7/1973 | Belzer et al. | .............................. 374/43 |
| 4,713,612 | 12/1987 | Takamine | .................................. 374/44 |
| 4,734,641 | 3/1988 | Byrd, Jr. et al. | .......................... 374/44 |
| 4,840,495 | 6/1989 | Bonnefoy | .................................. 374/43 |
| 4,861,167 | 8/1989 | Lobo et al. | ................................ 374/44 |
| 5,039,228 | 8/1991 | Chalmers | .................................. 374/57 |
| 5,302,022 | 4/1994 | Huang et al. | ............................. 374/43 |

FOREIGN PATENT DOCUMENTS

| 0224968 | 7/1985 | Germany | ................................. 374/43 |
| 0161649 | 12/1981 | Japan | ...................................... 374/43 |
| 0195145 | 11/1983 | Japan | ...................................... 374/43 |
| 0697894 | 11/1979 | U.S.S.R. | ................................. 374/43 |

*Primary Examiner*—Diego Gutierrez
*Attorney, Agent, or Firm*—McDonnell Boehnen Hulbert & Berghoff

[57] ABSTRACT

A method for evaluating the thermal impedance of packaged semiconductor chips. A measuring apparatus includes a thermostatic bath filled with a dielectric liquid and a temperature sensor for measuring the temperature of the bath. The semiconductor chip is subjected to a calibration step followed by a thermal response measurement step. Increasing the power pulse length allows measurement of the steady-state junction-to-case thermal resistance. The measuring apparatus and method is further used for tracing in-situ degradation of packaged semiconductor chips due to power cycling.

6 Claims, 5 Drawing Sheets

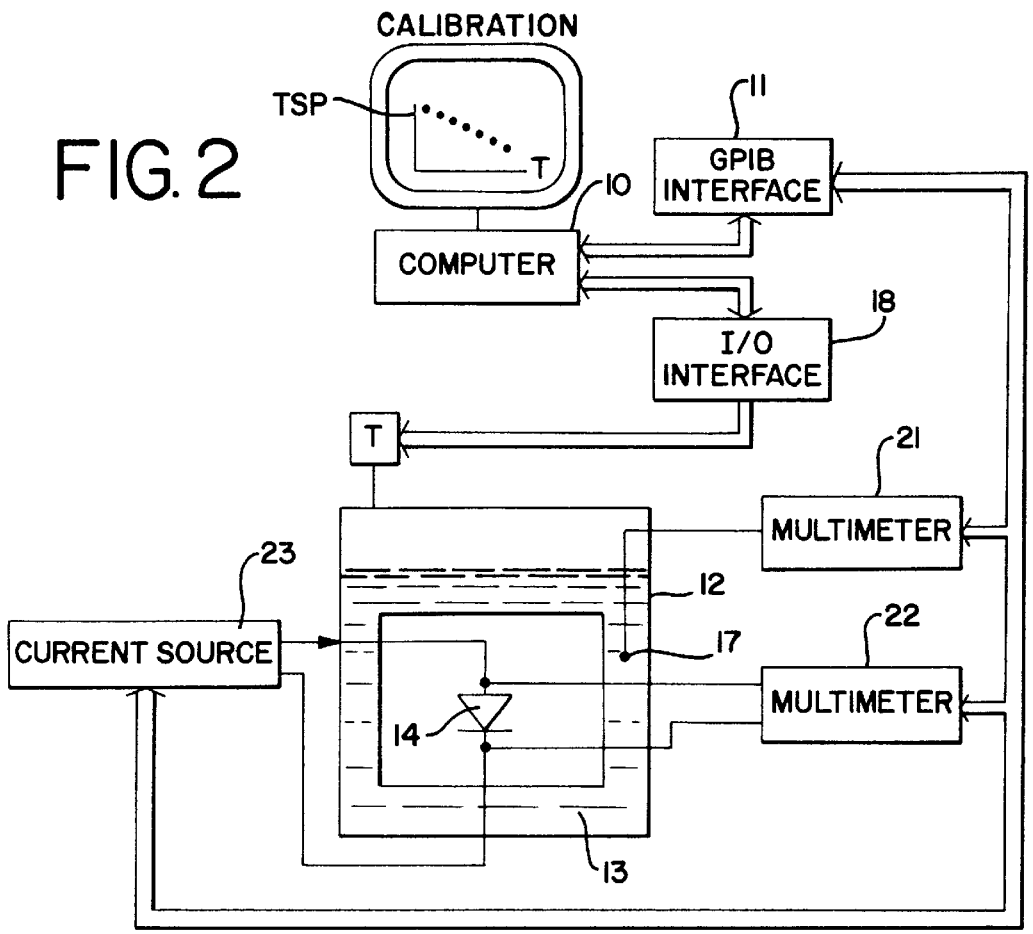
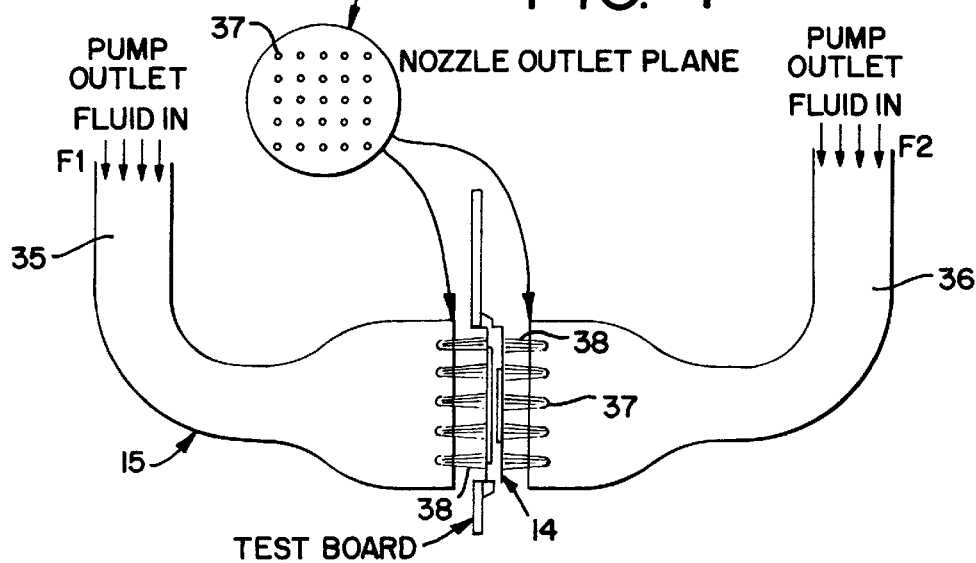

METHOD FOR THERMAL IMPEDANCE EVALUATION OF PACKAGED SEMICONDUCTOR COMPONENTS

This application is a divisional of U.S. application Ser. No. 08/543,867, filed Oct. 19, 1995, issued as U.S. Pat. No. 5,795,063 which claims priority benefits under 35 U.S.C. §119 based upon Belgian Patent application No. 09400949, filed on Oct. 19, 1994, and U.S. provisional application Ser. No. 60/003,899, filed on Sep. 18, 1995.

FIELD OF THE INVENTION

The present invention relates to an apparatus and method for measuring the thermal impedance of packaged semiconductor chips.

BACKGROUND OF THE INVENTION

The operating temperature is one of the most important factors affecting the reliability and performance of semiconductor chips. Large scale integration of integrated circuits leads to a higher power density, and means more and more heat dissipation per surface area of the semiconductor chip. Materials, packages, processing and cooling methods of semiconductor chips have to meet strong requirements to keep the operating temperature below a critical junction temperature specified by the manufacturer and which must not be exceeded or failure of the semiconductor chip will occur. Especially high technology and power devices must effectively transfer heat to the ambient.

Thermal performance of packaged semiconductor chips is traditionally expressed by the steady-state junction-to-case thermal resistance between junction and some reference location at the package. The thermal resistance is defined as $R_n=(T_j-T_{ref})/P$, wherein $T_j$ denotes the highest chip temperature further referred to as the junction temperature, $T_{ref}$ is some reference temperature at the package, and P denotes the electrical power being dissipated in the semiconductor chip. Standard measurement procedures such as SEMI G30-88, SEMI G43-87, MIL-STD-883C, Method 1012 should maintain consistent and repetitive results. These methods offer a choice of using either a fluid bath or a heat-sink environment and both assume that the measured thermal resistance is independent of such environmental choice. Unfortunately, the environmental conditions (e.g. flow field in fluid bath, circulation rate) may strongly influence the measured junction-to-case thermal resistance. As a result, strong differences in thermal resistance can be measured when using the same standard method in different environmental conditions. Moreover, according to the mentioned standards, the reference temperature is measured using a thermocouple in contact with the package surface. Attachment of a thermocouple heavily disturbs the heat transfer between package and environment. Large system disturbance errors are thus introduced in the measurement chain, resulting in huge uncertainties of the actual thermal resistance value.

As the reliability of semiconductor chips does not only depend on the steady-state temperature, but also on temperature changes and gradients, measurement of the transient thermal behaviour of semiconductor chips has gained increasing importance. The thermal impedance, defined as the transient thermal resistance, contains a lot of information concerning the semiconductor chip integrity and chip attach quality. Thermal impedance measurement techniques are described in MIL-STD-750C for various devices, such as diodes and transistors. The environmental conditions are not specified, though it is assumed that the package reference location is kept at a constant temperature.

There are disclosed in "Journal de la Physique, Part 3, Number 3, April 1993, Paris, of Pierre Paris, Jean-Marie Hausonne et Jean Lostec, for "Appareil permettant la caractérisation thermique de substrats et matériaux à forte conductibilité pour micro-électronique" an apparatus and method for characterising the thermal conductivity of substrates used in semiconductor packaging. This method is limited to measure the thermal properties of ceramic substrate samples and cannot be applied to packaged semiconductor chips.

U.S. Pat. No. 4,840,495 describes a method and apparatus for measuring the thermal resistance of a chip assembly including a semiconductor chip which is glued on a substrate. This method requires the semiconductor chip be accessible at the heat source side. Though, in a lot of applications a semiconductor chip is enclosed in some type of package which prevents a direct contact at the chip heat source. Thus it is not possible, with the methods of the prior art, to measure the thermal resistance of fully packaged semiconductor chips.

Due to the inaccessibility of the packaged semiconductor chip, an indirect but non destructive method is used to determine the junction temperature, which is defined as highest temperature. Temperature sensitive electrical parameters on the chip can be used as thermometers for indirect sensing of chip temperature.

OBJECT OF THE INVENTION

It is an object of the present invention to provide a solution for the aforementioned problems and to provide an apparatus and a method for accurate and reproducible measurement of the thermal impedance of packaged semiconductor chips, particularly with a high circuit density.

SUMMARY OF THE INVENTION

Accordingly, there is provided to the present invention an apparatus for evaluating the thermal impedance of a packaged semiconductor chip with a high circuit density, remarkable in that said apparatus comprises a thermostatic fluid bath, provided for a uniform, stable and accurate thermal boundary condition and at least one measuring unit for measuring the temperature of the fluid of said bath. The invention thus makes it possible to measure all or part of the thermal path of a packaged semiconductor.

It is further object of the present invention to provide a method and apparatus for in-situ monitoring of the presence and growth of defects in the semiconductor chip and package under power cycling.

According to a further embodiment of the invention, said at least one measuring unit is formed by a temperature sensor for measuring the temperature of the fluid in said bath; and said apparatus further comprises means for adjusting the temperature of said bath; means for measuring the value of a temperature sensitive electrical parameter of the semiconductor chip being evaluated; means for forcing a small current to allow measurement of said temperature sensitive electrical parameter; means for dissipating electrical power in said semiconductor chip; switching means for switching said power rapidly on and off; means for measuring the value of said electrical power; and means for monitoring and storing the value of said temperature sensitive electrical parameter as a function of time.

According to a preferred embodiment of the invention, said thermostatic bath is filled with a dielectric fluid and more particularly, said dielectric fluid is a silicon oil or FLUORINERT liquid with boiling point above 100° C. and pour point less than −25° C.

More specifically, the present invention aims at solving the problems related to the mentioned standard methods for measuring the steady-state and transient thermal performance of semiconductor chips. According to a further preferred embodiment of the present invention, the apparatus therefor further comprises a pump means for recirculating said fluid in said bath. Therewith, a uniform, reproducible, stable, and accurate thermal boundary condition can be created and achieved for the packaged chip as well during calibration of the temperature sensitive electrical parameter as during the actual thermal response measurement.

According to a variant of the present invention, said apparatus further comprises means to create one or more impinging liquid jets that are directed with a predetermined angle, preferably substantially perpendicular, relative to the surfaces of the packaged semiconductor chip being evaluated. Therefore, an appropriate submerged liquid jet impingement cooling scheme has been constructed.

In connection with said circulator pump, the required fluid outlet velocity can be achieved, and said one or more liquid jets impinging at one or more package surfaces can be created with a perfect reliability.

According to a preferred embodiment of the latter, said liquid jet creating means comprises at least one nozzle.

According to a further preferred embodiment thereof, the number and diameter of said nozzles, said capacity of said pump is chosen to ensure that the external temperature drop between package and fluid never exceeds a pre-determined value. The convective heat transfer between fluid and package is characterised by such high heat transfer coefficients, that the package surface is quasi-isothermal and its temperature always approximates the liquid temperature. Measurement of the liquid temperature can be performed by an accurate platinum resistance thermometer, without disturbing the heat transfer between package and liquid.

A measuring apparatus for performing the method according to a preferred combination in the present invention is remarkable in that it includes said thermostatic bath unit with said circulator pump and liquid jet impingement construction, and filled with a dielectric liquid, the liquid temperature being measured with a temperature sensor, a current source to supply the small calibration current during calibration and thermal response measurement, a power supply to dissipate the power during thermal response measurement, a digital storage oscilloscope or multimeter to capture and store the response of the temperature sensitive electrical parameter, and a wave form generator or I/O interface to rapidly apply and remove the power pulse to the chip under test.

In a method for measuring the thermal impedance of packaged semiconductor chips by means of an apparatus according to the present invention, there are comprised the steps of immersing the packaged semiconductor chip in a bath filled with a dielectric liquid; calibrating an on-chip temperature sensitive electrical parameter; and a thermal response measurement.

More specifically, said calibrating step is carried out by controlling the temperature of said liquid over a range of pre-set temperature values and recording the value of the temperature sensitive electrical parameter and the value of the liquid temperature when thermal equilibrium is reached at each temperature setpoint, and wherein an electrical power pulse is dissipated in the semiconductor chip during said thermal response measurement step.

Still further, said electrical power is measured; the value of the temperature sensitive electrical parameter is monitored and stored as function of time during and/or after the application said of power pulse; and wherein the response of said temperature sensitive electrical parameter is converted into a temperature response using the data obtained in the calibrating step.

It can further specifically be provided that said temperature sensitive electrical parameter yields the highest temperature of the semiconductor chip.

According to an advantageous embodiment of the method in the present invention, said temperature sensitive electrical parameter is chosen in such a way to obtain a linear relationship between said temperature sensitive electrical parameter and temperature.

Another drawback of the traditional methods described in the mentioned standards is their limitation to momentary evaluation of the thermal resistance, i.e. the evolution in time due to power or temperature cycles cannot be monitored using the same equipment. The traditional methods require the test chip to be transferred to another apparatus in order to subject it to temperature cycles.

According to a preferred embodiment of the method of the invention, it further comprises the step of monitoring in-situ thermal degradation of the packaged semiconductor chip by alternating the calibration and thermal response measurement step with a power cycling step. The measurement method can thus be applied more particularly for measuring in-situ thermal degradation in the semiconductor chip and package due to power cycling. Power cycles induce temperature cycles which may affect on-chip electrical parameters and cause defects such as cracks, voids, delamination in the semiconductor chip and package.

The method of the present invention thus allows power cycling and thermal impedance evaluation using the same apparatus. Changes in thermal impedance can be monitored in-situ during a long period of thermal loading. A temperature cycle is induced by heating the semiconductor junction region for a short period, followed by thermal equilibrium at the liquid temperature. After a certain number of such cycles, a thermal impedance measurement is performed. The present invention can thus be used to monitor the thermal degradation of semiconductor chips.

More specifically, said power cycling step includes the application of a pulsed power signal. The transient thermal impedance is an extremely important characteristic of a semiconductor chip. It contains a lot of information about the thermal properties of the semiconductor chip and chip attach region. Due to the difference in thermal time constants of the semiconductor chip and the package, the thermal impedance is much more sensitive to the presence of voids and cracks than the steady-state thermal resistance. The chip thermal time constant is generally some orders of magnitude smaller than that of the package. By heating the device with a power pulse, short enough such that the heat energy only has the time to flow through the chip and into the chip attach area, the temperature rise includes only the chip and chip attach resistance. In addition, for devices working under pulsed power operation conditions, it is the transient thermal impedance which determines by how much and for how long the DC power dissipation level of the device can safely be exceeded.

According to a further preferred embodiment, the amplitude, period and duty cycle of said power signal form is chosen in such a way to get the maximum junction temperature near a critical temperature, and to allow thermal equilibrium between successive power pulses.

In the present invention, the thermal performance is determined by two important characteristics, the steady-state thermal resistance between junction and (quasi)-isothermal case, and the thermal impedance when a heating pulse is applied to the junction region of the semiconductor chip. In the present method according to the invention, the steady-state thermal resistance between junction and case is obtained by increasing the heating pulse duration length until the junction temperature reaches equilibrium.

In order to create a large temperature difference between package and junction which exceeds a pre-determined value, the power cycling step preferably further comprises the step of controlling the fluid temperature at a low value e.g., between −50° C. and 0° C.

In a preferred mutual combination, the method of measurement of thermal impedance according to the invention is remarkable in that it comprises a calibration step to derive the relationship between an on-chip temperature sensitive electrical parameter and temperature, being performed by immersing the packaged semiconductor chip in a thermostatic bath with circulator pump and filled with a dielectric liquid, thereby providing a perfectly stable, uniform and accurate temperature chamber. The method of measurement of thermal impedance according to the invention is further characterised in that it comprises a thermal response measurement step while the semiconductor chip is immersed in the fluid bath and cooled by one or more impinging liquid jets, comprising the application of a power pulse, removal of the power pulse, capturing and storing of the temperature sensitive electrical parameter during heating and/or cooling down, coverting the response of this parameter to temperature using the previously derived calibration relationship, and calculating the thermal impedance from the junction thermal response, the measured liquid temperature, and measured heating power.

According to a further embodiment according to the invention it can be used for monitoring in-situ change of thermal impedance due to thermal degradation, by alternating a certain number of power cycles in the semiconductor chip with a thermal impedance measurement, without the need for supplementary apparatus.

Further features and advantages of the invention will become clear from the detailed description of an exemplary embodiment, in conjunction with the drawings.

BRIEF DESCRIPTION OF THE DRAWINGS

FIG. 2 represents a block diagram similar to that of FIG. 1, showing an apparatus for the calibration step of the temperature sensitive electrical parameters according to the present invention.

FIG. 4 is a graph representing a liquid jet impingement construction used to create one or more parallel impinging liquid jets on the main surfaces of the packaged semiconductor chip according to a variant of the present invention.

DESCRIPTION OF THE PREFERRED EMBODIMENT

Figure 1:
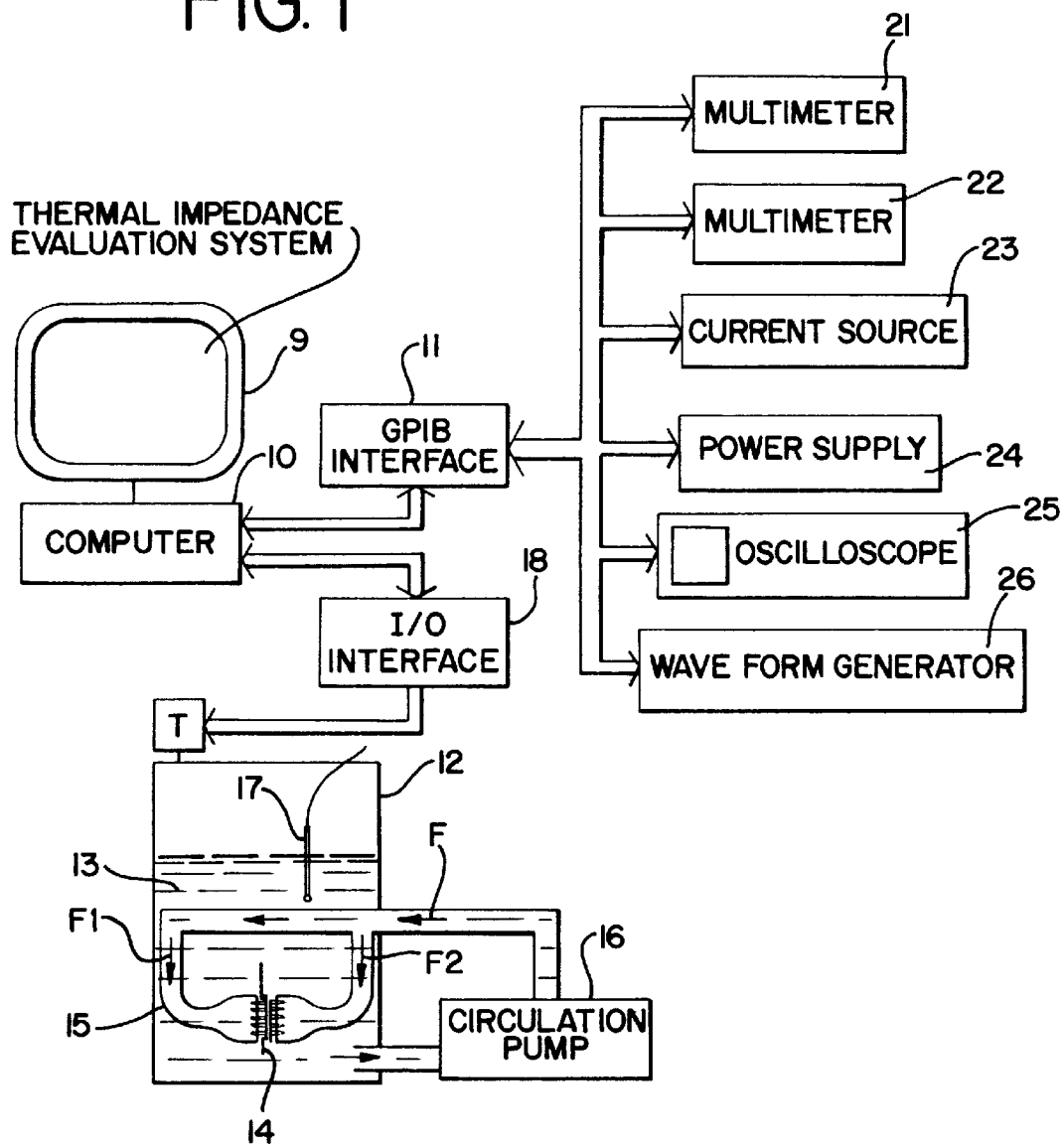
FIG. 1 represents a block diagram of a set-up apparatus according to an embodiment of the present invention.

The apparatus for the measurement set-up as schematically shown in FIG. 1, wherein 9 represents a thermal impedance evaluation system, comprises a processing unit, e.g. a computer 10, that may be equipped with instrument control software, and connected to the measurement and control instruments by means of a GPIB interface 11. A thermostatic fluid bath 12 is included in the apparatus. The bath vessel is filled with a dielectric fluid 13, such as silicone oil or a FLUORINERT liquid. Preferably, a fluid with a boiling point above 100° C. and a pour point below −25° C. is selected. An I/O interface 18 is used for controlling the setpoint of the thermostatic bath. Said bath 12 serves as a controlled temperature environment capable of maintaining the whole semiconductor chip and package 14 within +/− 0.1° C. of the liquid temperature during calibration step of the temperature sensitive electrical parameters. The semiconductor chip 14 is immersed in said liquid 13, and is surrounded by a liquid jet impingement construction 15, comprising a tubing system 35, 36 and one or more nozzles 37 which are directed towards one or more package surfaces. A circulator pump 16 provides the required flow rate indicated by the direction of arrow referenced with F to obtain one or more high velocity impinging liquid jets 38 on the package surfaces of the semiconductor chip 14. The liquid temperature is measured using a temperature sensor 17, which may be a platinum thermometer.

A multimeter 22 is destined to read the value of the temperature sensitive electrical parameter during the calibration step, and the value of the heating voltage and heating current during the power pulse application of the thermal response measurement step. The second multimeter 21 reads the output of the temperature sensor 17 during the calibration and thermal response step.

Figure 3:
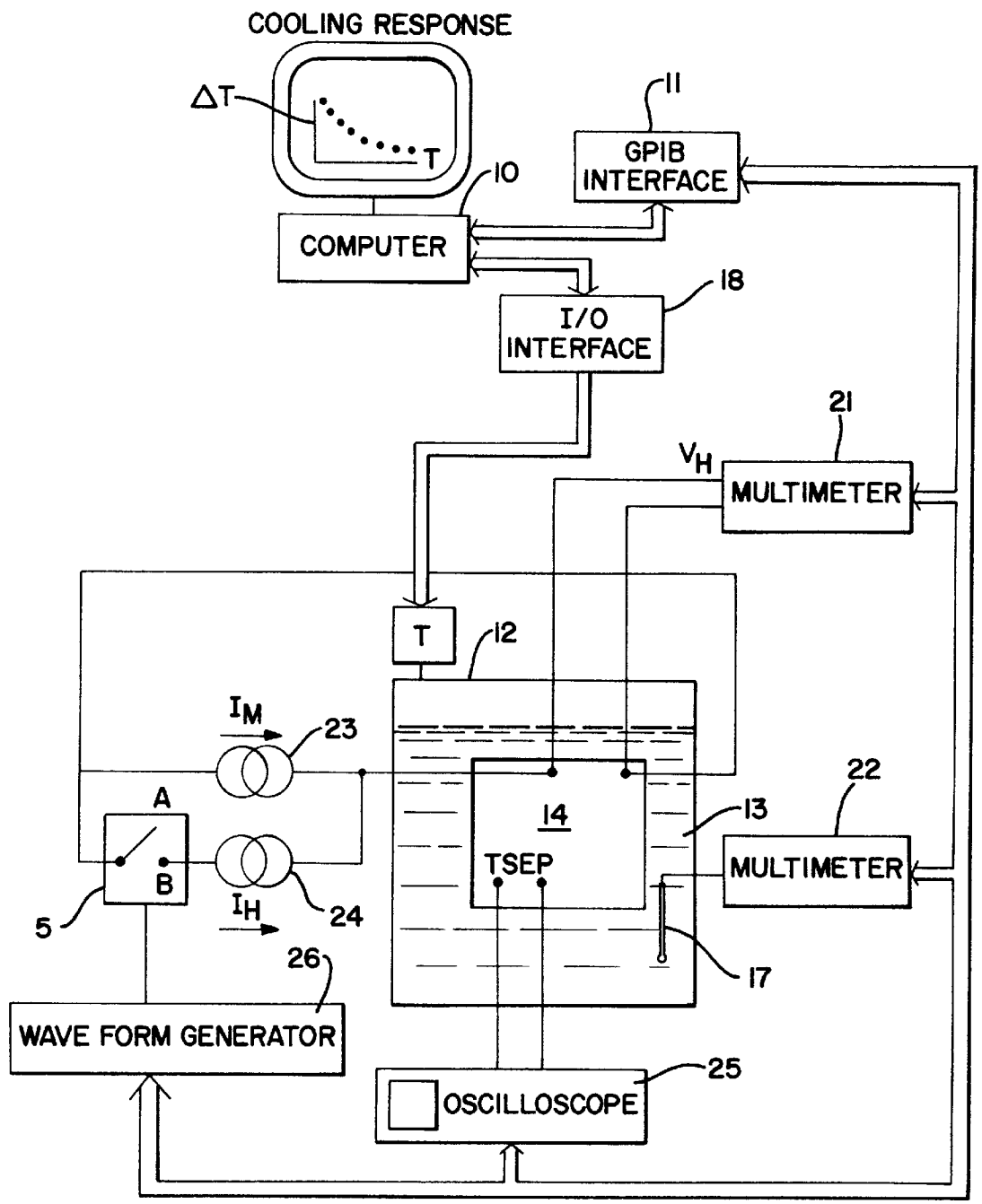
FIG. 3 represents a block diagram of a measurement set-up apparatus according to a further embodiment of the present invention for the thermal response measurement step.

A constant current source 23 is also included in the apparatus. This current source provides a fixed small current during the calibration and thermal response measurement, as shown in FIG. 2 and 3. The current is set in the range 100 $\mu$A to 100 mA.

A power supply 24 provides the heating power in the semiconductor chip under test during the thermal response measurement step.

As shown in FIG. 3, an electronic switch 5 issued to apply and remove the heating power during the thermal response measurement step, or during an aging test. This electronic switch is controlled by a waveform generator 26 or an I/O interface.

In order to record the temperature sensitive electrical parameter as function of the time during heating and/or cooling of the semiconductor chip, a digital storage oscilloscope 25 or digital storage multimeter is included in the apparatus.

The described instruments 21 . . . 26 are controlled by the computer over a GPIB-interface 11. The measured data is read and stored for post-processing purposes.

The method of thermal impedance measurement according to the present invention consists of two major steps: a calibration step and a thermal response measurement step.

The calibration step is performed by immersing the packaged semiconductor chip under test in the thermostatic bath 12 that acts as a temperature controlled environment. During this calibration step, the temperature of the semiconductor chip is externally governed by the liquid, the value of the temperature sensitive electrical parameter is measured and recorded at different pre-set temperature setpoints. The apparatus required for the calibration of the voltage drop of a forward polarised diode 14 is shown in FIG. 2.

During the thermal response measurement step, the device is heated for a certain time period by applying an electrical power pulse at the junction region of the semiconductor chip. The dissipated power is measured. Depending on the art of the temperature sensitive electrical parameter, its heating and/or cooling response is monitored as function of time on the digital storage oscilloscope 25 or multimeter. Then, the stored response of the temperature sensitive electrical parameter is converted into a temperature response according to the relationship derived in the calibration step.

The calibration is done by immersing the chip into a thermostatic bath, filled with a dielectric liquid. In order to characterise the transient thermal behaviour of semiconductor chips in an indirect way, an appropriate temperature sensitive electrical parameter inside the chip must be calibrated versus temperature. The temperature sensitive electrical parameter and the magnitude of the calibration current shall be chosen so that the value of the parameter is a linear function over the normal operating temperature range of the chip. In addition the electrical parameter should yield the maximum temperature inside the chip. Useful temperature sensitive electrical parameters are the forward diode voltage for power diodes, base-emitter voltage for bipolar transistors, source-drain diode voltage or gate-source threshold voltage for MOSFETs.

The temperature of the bath is varied over a certain range, e.g. 10–100° C. A thermostatic bath is the most accurate kind of controllable temperature environment.

Once the value of the temperature sensitive electrical parameter has stabilised, the temperature of the dielectric liquid is measured, e.g. by a platinum resistance thermometer and the value of the temperature sensitive electrical parameter is recorded. The data is automatically regressed and the correlation coefficients are stored in a file directly accessible to the control software during subsequent response measurement. During the calibration step, the heat dissipation in the chip has to be minimised to be sure that the internal temperature is equal to the liquid temperature. This can be accomplished by choosing the measurement current in the range 100 μA for small devices to 100 mA for larger ones.

Figure 5:
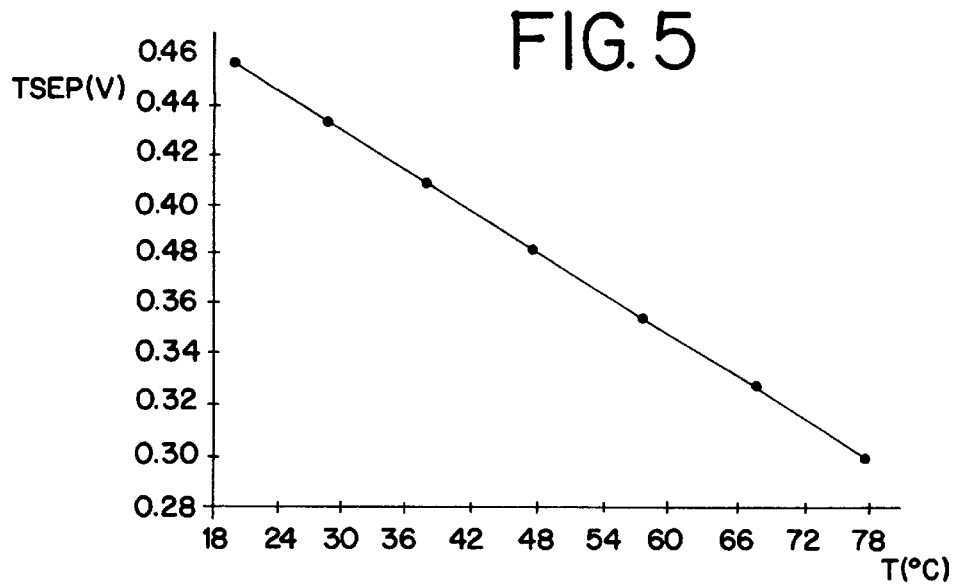
FIG. 5 and 8 represent typical calibration curves obtained by the measurement system related to the present invention.

FIG. 5 shows the calibration curve for the forward polarised base-emitter voltage of an npn bipolar transistor as function of temperature. This curve was constructed for a calibration current equal to 100 μA and represents a linear relationship between temperature sensitive electrical parameter TSEP and temperature T. The collector-base voltage was set to 15V.

Figure 8:
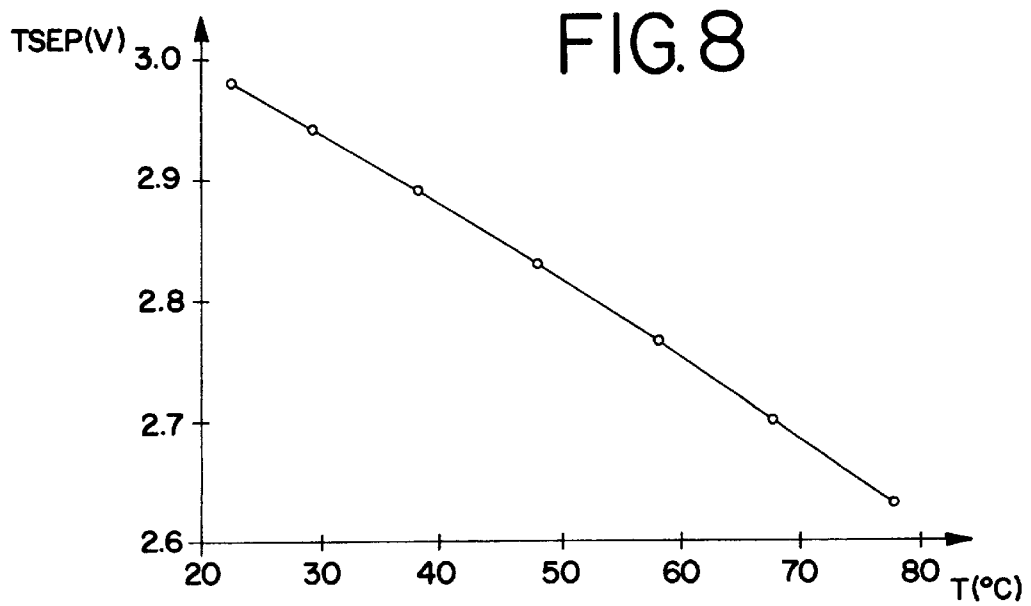

FIG. 8 shows an analogue calibration curve for the gate-source voltage versus temperature for an N-channel TMOS power FET transistor. The calibration drain-source current is 100 μA. The drain-gate voltage was set to 15V.

FIG. 3 represents the measurement set-up for the thermal response measurement step. The chip under test 14 is immersed in the thermostatic fluid bath 12 while the liquid temperature is maintained at a pre-set value. The liquid is recirculated in the bath by means of a pump.

The packaged semiconductor chip is cooled by one or more submerged impinging liquid jets, using a construction as shown in FIG. 4. One or more impinging liquid jets 38 are directed perpendicular to the surfaces of the packaged semiconductor chip 14 under test. One or more nozzles 37 in the outlet plane 39 increase the outlet velocity to obtain the liquid jets 38. The convective heat transfer between fluid and package is characterised by such high heat transfer coefficients, that the package surface is quasi-isothermal and its temperature approximates the liquid temperature. The number and diameter of said nozzles 37, and capacity of said pump is chosen to ensure that the external temperature drop between package and fluid never exceeds a pre-determined value. The reference package temperature is then obtained by measuring the controlled liquid temperature. Measurement of the liquid temperature can be performed by an accurate platinum resistance thermometer, without disturbing the heat transfer between package and liquid.

For obtaining large heat transfer coefficients at a surface the use of one or more impinging jets is involved.

Convective heat transfer coefficients of the order of 10,000 W/m$^2$ may be achieved using liquid impinging jets. These high convective heat transfer coefficients are well-suited to improve the thermal characterisation of electronic packages in a fluid bath environment. A big advantage of impingement cooling is the small external temperature difference between case and fluid. A simple calculation, assuming a heat transfer coefficient of 40,000 W/m$^2$K shows that the external convective thermal resistance for a 2 cm by 2 cm surface area is as low as 0.0625 K/W, which is much smaller than the experimental measurement accuracy obtained by the actual $R_{je}$ standard methods. In order to find the optimal nozzle outlet configuration, i.e. number of parallel nozzles, nozzle diameter φ, and nozzle-to-package separation distance, a fundamental understanding of the hydrodynamic and thermal conditions of an impinging jet flow is required.

Liquid jet impingement cooling schemes can be divided into two categories: free surface jet impingement and submerged jet impingement. A free surface jet is discharged into an ambient gas, while a submerged jet is discharged into a stagnant fluid of the same type. These two types of impinging jets significantly differ in their hydrodynamic and thermal performance. A free surface jet flow is characterised by a very small shear stress at the liquid/gas interface. In the absence of gravitational acceleration, the jet diameter and the nozzle exit velocity are preserved until impingement on the target surface. This hydrodynamic behaviour causes the convective heat transfer between fluid and surface to be independent of the nozzle-to-surface separation distance. A submerged liquid jet is characterised by a shear layer between jet and the surrounding fluid. Experiments with both water and FC-77 have shown that the convective heat transfer coefficient is higher for a submerged jet with S/d=3 than for a free surface jet, for $Ra_4$>4000. The higher Nusselt numbers obtained with the submerged jet can be attributed to heat transfer enhancement by turbulence generated in the free shear layer of the jet. For submerged jets, the Nusselt number (and heat transfer coefficient) is quasi independant of S/d for 1<S/d<4. This can be explained by the fact that, for 1<S/d<4, the heat source is still located within the potential core of the jet. Furthermore the Nusselt number decreases with increasing S/d ratio for large separation distances. The highest heat transfer coefficients are thus obtained for submerged jets and small S/d values, i.e. S/d≦4.

For an unconfined, submerged circular jet, the local and average convective heat transfer coefficients are affected by nozzle exit volocity profile, jet turbulence, jet Reynolds number, nozzle-to-surface distance, and the size of the target surface. At this point, the ratio S/d is set at a fixed value S/d=4 . . . 5. The size of the target surface depends on the chip and package size. To be useful for most package types, a heater surface with length L=25 mm is presumed. Several correlations for the average Nusselt number are available in literature. Womac et al. proposed an area-weighted combination of correlations for the two surface regions; the impingement region was assumed to extend to a radius of 1.9 and to be followed by transition to a turbulent wall jet region.

$$NuL/Pr^{0.4}=C_1 \ Red \ m \ L/d \ A_T+C_2*L/L*(1-A_T) \qquad (4)$$

where $$A_T=\pi(1.9d)^2/L^2 \qquad (5)$$

m=0.5
n=0.8
$C_1$=0.785
$C_2$=0.0257 and L* denotes the average length of the wall region:

$$L*=0.5 \ (1+\sqrt{2})L-3.8d/2 \qquad (6)$$

For multiple, unconfined submerged jet configurations, the same correlation can be used to calculate the average convective heat transfer coefficient. In this case, the length L in equations (4), (5) and (6) has to be replaced by the pitch P between the nozzles. The use of multiple jets has the potential to maintain a greater degree of temperature uniformity across the surface. Though jet interactions may influence the local heat transfer conditions.

Figure 6:
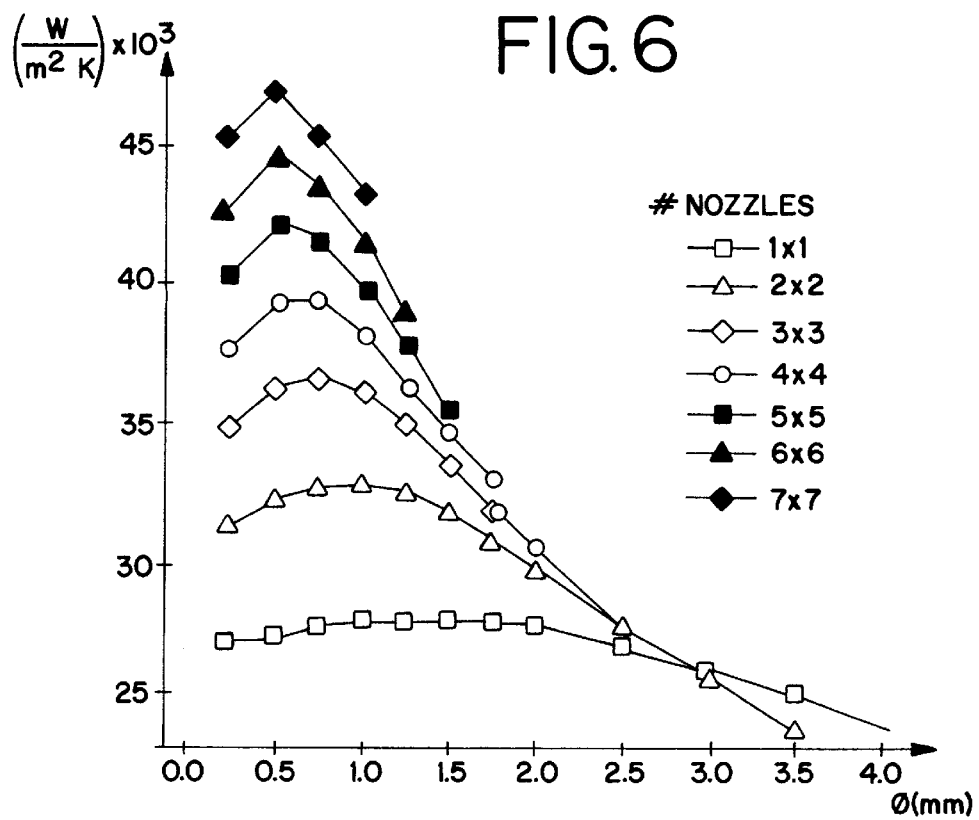
FIG. 6 and 7 show curves representing average convective heat transfer coefficient as function of the number of outlet nozzles and nozzle diameter with as working fluids water, and FC-76, respectively.
Figure 7:
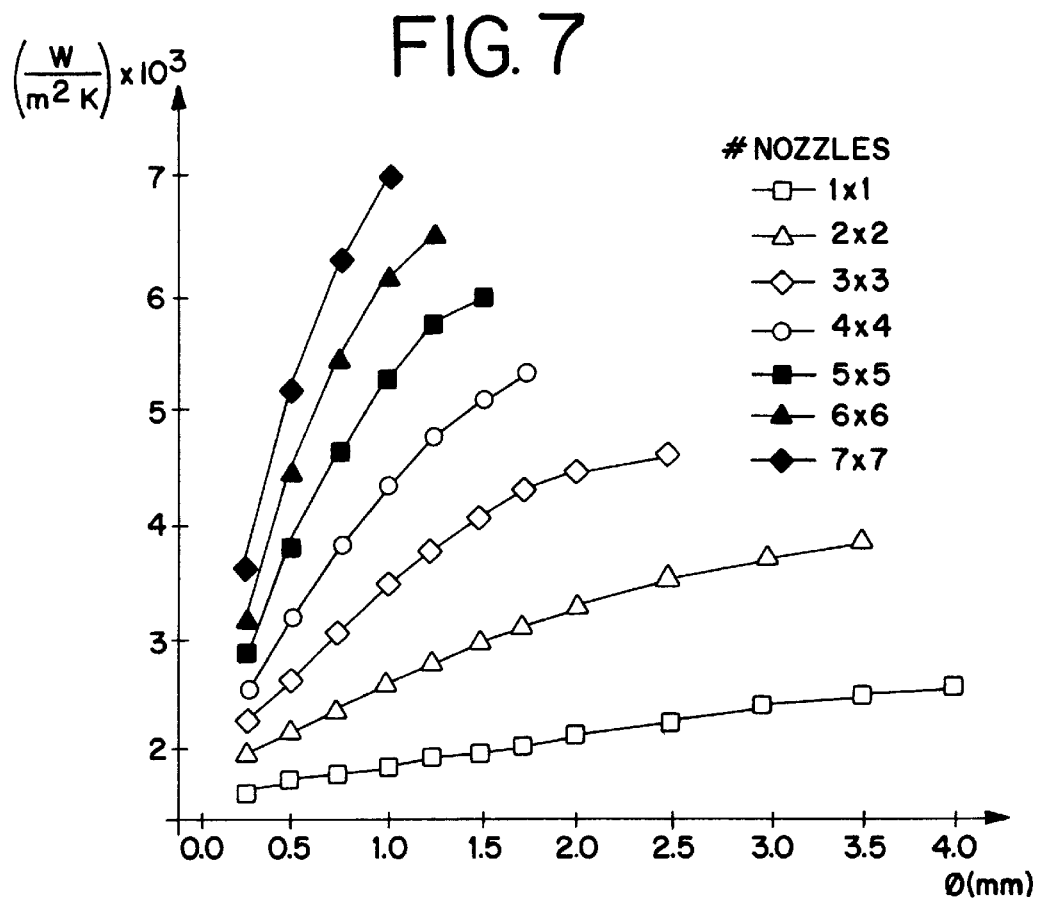

The Womac correlation (4) for single and multiple unconfined circular jets was then used to calculate the optimal number or parallel jets and the optimal nozzle outlet diameter. The actual flow rate was determined as the intersect of the circulation pump characteristic (thermostatic bath) and the load curve of the tubes and nozzle contractions. The outlet flow rate of the circulation pump is split into two parallel flows which are impinged perpendicular to the top and bottom surfaces of the package. A schematic view of the proposed mounting arrangement is given in FIG. 4. The optimal nozzle diameter φ of both water and FC-70 can be obtained from the graphs in FIGS. 6 and 7, showing each in the upper right corner the amount of nozzles for each corresponding symbol.

It appears that water has much better thermal properties than FLUORINERT liquids. When using water as the cooling fluid, heat transfer coefficients in the order of 40,000 W/m²K can be obtained for an array of 5×5 nozzles with diameter=0.5 mm. Also for FLUORINERT FC-70, an array of multiple small nozzles yields the highest heat transfer coefficients. The optimal nozzle outlet diameter is somewhat larger than for water; and the accompanying average heat transfer coefficient is about ten times smaller. Though, comparing to an initial value of about 100 to 200 W/m²K, the heat transfer coefficient has increased significantly and more important, the flow field is well-defined, resulting in reproducible values for $R_{jm}$ which will approximate $R_{jc}$. The graphs below were calculated for a circulation pump with a maximum flow rate of 15 liter/min and maximum pressure drop of 480 mbar.

The thermal response measurement step starts with the adjustment of the heating current $I_H$ and the measurement current $I_M$, which must be equal to the calibration current. The value of $I_H$ is usually at least two orders of magnitude greater than the value of $I_M$.

An electronic switch 5 allows one to rapidly apply and remove the heating current from the test chip, while the small measurement current $I_N$ is always flowing. The switch 5 can take two positions: an open position A and a closed position B. The position of switch 5 is controlled by a wave from generator 26 or I/O interface. When the switch is in open position A, the value of the temperature sensitive electrical parameter is measured which provides the initial device temperature. Then the device is heated for a short period of time, by switching the switch 5 to the closed position B. The dissipated power is measured as the product of the heating current $I_H$ and the heating voltage $V_W$ resulting from application of this current. After an adjustable pulse duration, the switch 5 is again moved to the open position A and the heating and/or cooling response of the temperature sensitive electrical parameter is stored in memory of the digital storage oscilloscope 25 or multimeter. Next, the response of the temperature sensitive electrical parameter is converted into a temperature response using the calibration curve.

The invention thus represents a non-destructive and reproducible test method to evaluate the stead-state and transient thermal performance of electronic chips. The measurement procedure related to the present invention allows a qualitative evaluation of the mechanical integrity of the semiconductor chip and chip attach based on the thermal characteristics.

In addition, the described apparatus offers the possibility to trace aging of electronic chips due to power and temperature cycling. To realise a cyclic thermal load, a power pulse is applied to the semiconductor chip while it is immersed in a thermostatic fluid bath. In order to create a large temperature difference between package surface and the semiconductor junction during power dissipation, the temperature of the bath is kept at very low temperature, e.g. −25° C., using the submerged impingement construction. The power dissipation has to be adjusted as high as the junction temperature reaches its maximum specified operating temperature. This induces a thermal load cycle, creating a large thermal mismatch between the different layers of the packaged semiconductor chip. After this power pulse, the junction region of the chip is allowed to reach thermal equilibrium with the fluid. The power and temperature cycle can now be repeated. Those power cycles can be alternated with thermal impedance measurements, consisting of calibration step and thermal response measurement step as described previously.

Alternating the power cycles at regular time intervals with a thermal impedance measurement provides the in-situ change of thermal impedance, and allows investigation of the aging kinetics under thermal load condition.

A remarkable advantage of the present invention is the minimal requirement of knowledge and experience about the measurement set-up due to the fact that all measurements are completely controlled by the operating software. Initialisation and configuration of the instrumentation system is done automatically.

Furthermore, the thermostatic bath with submerged liquid jet impingement scheme creates a very stable, uniform, reproducible and accurate temperature chamber. This allows a very accurate calibration of the temperature sensitive electrical parameters and accurate knowledge of the package reference temperature during thermal response measurement.

We claim:
1. A method for determining the thermal impedance of a packaged semiconductor chip, the method comprising the steps of:

immersing said packaged semiconductor chip in a dielectric fluid;

determining calibration values of a temperature sensitive electrical parameter of said chip.

applying at least one electrical power pulse to said packaged semiconductor chip;

measuring said electrical power pulse;

recording a plurality of measured values of said temperature sensitive electrical parameter;

converting said pluarlity of measured values into a temperature response characteristic using said calibration values; and calculating the thermal impedance using at lest said measured electrical power pulse and said temperature response characteristic.

2. The method of claim 1 wherein said temperature sensitive electrical parameter is selected such that a calibration value of said temperature sensitive electrical parameter is determined at the highest temperature of said packaged semiconductor chip.

3. The method of claim 1 wherein said calibration values of said temperature sensitive electrical parameter vary in a predominantly linear manner as a function of temperature.

4. A method for determining the thermal impedance of a packaged semiconductor chip comprising the steps of:

immersing said packaged semiconductor chip in a dielectric fluid;

determining calibration values of a temperature sensitive electrical parameter of said chip;

determining measured values of said temperature sensitive electrical parameter by performing a thermal response measurement on said chip while creating at least one fluid jet flow impinging on said chip; and calculating the thermal impedance using at least said calibration values and said measured values of said temperature sensitive electrical parameter.

5. The method of claim 4 wherein said fluid jet flow is applied through at lest one nozzle.

6. The method of claim 5 wherein said thermal response measurement includes applying at lest one electrical power pulse to said packaged semiconductor chip.

* * * * *